United States Patent [19]

Yu

[11] Patent Number: 5,795,917
[45] Date of Patent: Aug. 18, 1998

[54] ENZYME INHIBITOR ACARICIDES I

[76] Inventor: Ida K. Yu, 2727 Marina Blvd., #208, San Leandro, Calif. 94577

[21] Appl. No.: 703,605

[22] Filed: Aug. 23, 1996

Related U.S. Application Data

[60] Provisional application No. 60/002,733 Aug. 24, 1995.
[51] Int. Cl.$^6$ ..................................................... A01N 37/52
[52] U.S. Cl. .................................................................. 514/634
[58] Field of Search ............................................... 514/634

[56] References Cited

PUBLICATIONS

The Merck Index, 11th Ed. (1989) p. 718 #4475.

*Primary Examiner*—Allen J. Robinson
*Attorney, Agent, or Firm*—Pennie & Edmonds LLP

[57] ABSTRACT

The invention provides novel methods of controlling mite infestations of plants. The novel methods employ the step of applying an effective amount of a compound that can inhibit the proteolytic activity of trypsin and trypsin-like proteinase. Preferred compounds for use in the subject methods are Pefabloc SC, pentamidine, soybean trypsin inhibitor, lima bean trypsin inhibitor, and aprotinin.

Another aspect of the invention is to provide formulations for use in applying to plants so as to control mites. The formulations comprise one or more inert carrier and a compound that can inhibit the proteolytic activity of trypsin. Preferred acaricidal compounds for use inclusion in the subject formulations are Pefabloc SC, pentamidine, soybean trypsin inhibitor, lima bean trypsin inhibitor, and aprotinin. Another aspect of the invention is to provide improved methods for the screening of compounds that have acaricidal activity. The screening method of the invention limits the range of compounds for screening to those compounds capable of inhibiting the proteolytic activity of trypsin and trypsin-like proteinases.

5 Claims, No Drawings

ENZYME INHIBITOR ACARICIDES I

This application is a provisional application of 60/002,733, filed Aug. 24, 1995.

FIELD OF INVENTION

This invention is in the field of agricultural acaricides, more particularly, in the field of acaricide specific for Tetranychus species.

BACKGROUND

Many species of mites are known to damage plants of agricultural importance. Mites that are known to be significant agricultural pests include those that belong to the families Tetranychidae, Tyroglyphidae, Glycyphagidae, Eriophydae, and Panonychidae. Mites belonging to the family Tetranychidae, such as *Tetranychus urticae* and *Tetranychus cinnabarinus*, are of particular commercial significance. It is of particular interest to prepare compounds that have acaricidal activity so as to prevent and reduce mite infestations. It is also of interest to provide improved methods of screening for compounds that have acaricidal activity.

SUMMARY OF THE INVENTION

One aspect of the invention is to provide for novel methods of controlling mite infestations of plants. The novel methods employ the step of applying an effective amount of a compound that can inhibit the proteolytic activity of trypsin and trypsin-like proteinase. Preferred compounds for use in the subject methods are Pefabloc SC, pentamidine, soybean trypsin inhibitor, lima bean trypsin inhibitor, and aprotinin.

Another aspect of the invention is to provide methods of controlling mite infestations by administering an effective amount of guanidine or derivatives thereof.

The formulations comprise one or more inert carrier and a compound that can inhibit the proteolytic activity of trypsin. Preferred acaricidal compounds for use inclusion in the subject formulations are Pefabloc SC, pentamidine, soybean trypsin inhibitor, lima bean trypsin inhibitor, and aprotinin. Guanidine, and derivatives thereof, may also be used as acaracides and in the acaracidal formulations of the invention.

An other aspect of the invention is to provide improved methods for the screening of compounds that have acaricidal activity. The screening method of the invention limits the range of compounds for screening to those compounds capable of inhibiting the proteolytic activity of trypsin and trypsin-like proteinase.

DESCRIPTION OF THE SPECIFIC EMBODIMENTS

The invention provided herein exploits the discovery that many compounds capable of inhibiting the proteolytic activity of trypsin have acaricidal activity against mites, especially the mite *Tetranychus urticae*.

One aspect of the invention is to provide novel methods of controlling mite infestations of plants. The term "controlling" as used with respect to mites, refers both to the prevention of mite infestations and to the reduction of the number of mites already present on a given plant suffering from a mite infestation. Thus compounds for use in the subject methods have acaricidal activity, i.e., the compounds can kill mites in relatively low concentrations. The compounds for use in the subject methods may have acaricidal activity against one or more of the three stages of the mite life cycle, i.e., the egg stage, the larval stage, and the adult stage. The acaricidal compounds for use in the subject method are inhibitors of the proteolytic activity of the enzyme trypsin. The term "trypsin" as used herein, refers to trypsin as produced in the pancreas of any of a variety of mammals. Thus the compounds for use in the methods of the invention may inhibit bovine trypsin, ovine trypsin, porcine trypsin, and trypsin-like enzymes. The term "trypsin-like" enzyme as used herein refers to a proteinase that has three-dimensional structural homology to the enzyme trypsin, particularly the catalytic triad present in trypsin. The term "trypsin inhibitor" as used herein refers to a compounds that interacts with trypsin and can significantly lower the turnover rate of a trypsin catalyzed proteolytic reaction. Many trypsin inhibitors are known to the person of ordinary skill in the art and can be found by referring to numerous publications such as the *Handbook of Enzyme Inhibitors*, 2nd Edition (ISBN 156081-219-2), and the like. Additionally, the invention contemplates the use of trypsin inhibitors that have not yet been identified or synthesized in the methods of the invention. The three dimensional structure of trypsin (and some trypsinlike enzymes) has been established and the person of ordinary skill in the art may design novel compounds that act as trypsin inhibitor by use of molecular modeling computer software. Additionally, compounds suspected of being trypsin inhibitors may readily be evaluated for their proteolytic inhibitory properties by measuring the effect of the suspected trypsin inhibitor on a trypsin catalyzed reaction. Preferred trypsin inhibitors for use in the subject methods are trypsin inhibitors that lack significant toxicity for humans and for plants to be treated by the subject methods. Not all inhibitors of trypsin proteolytic activity have acaricidal activity; however, trypsin inhibitors having acaricidal may readily be detected by screening trypsin inhibitors of interest in bioassays for toxicity to mites. Typically, such assays involve directly applying trypsin inhibitors of interest to either mite adults, larvae, or eggs and measuring the survival rate, or allowing mite adults or larvae to ingest trypsin inhibitors of interest and then measuring survival rates. Preferred compounds for use in the subject methods are Pefabloc, soybean trypsin inhibitor (type I-S), pentamidine, lima bean-trypsin inhibitor, and aprotinin. Although the methods of the invention may be used to control many different species of mites, the subject methods are particularly effective against *Tetranychus urticae*.

The invention also provides for the use of guanidine (iminourea $H_2NC(=NH)NH_2$) as a acaracide. The term "guanidine" as used herein refers collectively to all salts of guanidine; however, the use of guanidine hydrochloride is particularly preferred for use in the subject compositions and methods. The preparation of guanidine is described, among other places, in U.S. Pat. No. 2,762,843, U.S. Pat. No. 2,590,257, U.S. Pat. No. 3,009,949, and U.S. Pat. No. 3,108,999. A person of ordinary skill in the art of organic chemistry may make numerous derivatives of guanidine. Such guanidine derivatives may be readily assayed so as to determine which guanidine derivatives have acaracidal activity.

The methods of the invention comprise the step of applying a trypsin inhibitor having acaricidal activity or applying guanidine (or derivatives thereof) to a plant of interest. The acaricide may be applied by a variety of means such as spraying a liquid, dusting a powder and the like, well known to the person of ordinary skill in the art of crop protection. The particular method of application selected will be dependent upon a number of factors such as the type of plant, the formulation selected, the arrangement of plants in the field, weather conditions, and the like. The actual amount of acaracide applied to each plant may be varied so as to achieve the desired degree of pest control. The optimal dosage for a specific plant, specific mite species, and specific trypsin inhibitor, under a given set of environmental conditions may be determined through routine experimentation in which the dosage is systematically varied.

The methods of the invention preferably use the acaricidal trypsin inhibitor or guanidine (or derivatives thereof) in a formulation adapted for application to plants. The acaricidal trypsin inhibitors and guanidine for use in the subject methods will generally be used in formulation with a liquid or solid diluent or with an organic solvent. The invention specifically provides for numerous formulations comprising trypsin inhibitors and guanidine for use as acaricides on plants and a inert carrier, such as a diluent. The term "inert" is used to indicate that the carrier does not have significant acaricidal activity. The formulations of the inventions comprise an acaricidal trypsin inhibitor or guanidine (or derivatives thereof) and a diluent or surfactant, which may not act as an inert carrier. The formulations may further comprise additional compounds that have acaricidal activity. Useful formulations can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 35% surfactant(s) and b) about 5% to 99% solid or liquid inert diluent(s). More specifically, they will contain these ingredients in the following approximate proportions:

|  | Active | Percent by Weight | |
| --- | --- | --- | --- |
|  | Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–35 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers," 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, N.Y., 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publ. Co., Inc., New York, N.Y., 1964, list surfactants and recommended uses. All formulations can contain minor amounts of additives to reduce foam, caking, corrosion, microbiological growth, etc. Additives to protect the active compounds against light induced degradation, e.g., photoprotectants, UV screening compounds, and the like are also preferably included in the subject formulations. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon prefoamed granular carriers or by agglomeration techniques. See J. E. Browning, "Agglomeration," *Chemical Engineering*, Dec. 4, 1967, pp. 147ff and "Perry's Chemical Engineer's Handbook," 4th Ed., McGraw-Hill, New York, N.Y., 1963, pp. 8–59ff.

For more information regarding the art of formulation, see for example:

- H. M. Loux, U.S. Pat. No. 3,235,361, Feb. 15, 1966, Column 6, Line 16 through Column 7, Line 19 and Examples 10 through 41.
- R. W. Luckenbaugh, U.S. Pat. No. 3,309,192, Mar. 14, 1967, Column 5, line 43 through Column 7, Line 62 and Examples 8, 12, 15, 39, 41, 52, 53, 58, 132, 138–140, 162–164, 166, 167, 169–182.
- H. Gysin and E. Knusli, U.S. Pat. No. 2,891,855, Jun. 23, 1959, Column 3, Line 66 through Column 5, Line 17 and Examples 1–4.
- G. C. Klingman, "Weed Control as a Science," John Wiley and Sons, Inc., New York, N.Y., 1961, pp.81–96.
- J. D. Fryer and S. A. Evans, "Weed Control Handbook," 5th Ed. Blackwell Scientific Publications, Oxford, 1968, pp. 101–103.

Another aspect of the invention is to provide novel methods of screening for compounds that have acaricidal activity, especially acaricidal activity against Tetranychus species, particularly *Tetranychus urticae*. Conventional methods of screening compounds for acaricidal activity involve the use of relatively simple bioassays in which the toxicity of potential acaricidal is measured against mite eggs, larvae, or adults. A significant disadvantage of these previous screening methods is that the range of potential compounds for screening is virtually infinite. The improved methods of screening for acaricidal compounds described herein limits the potential range of compounds for screening to those compounds that are capable of inhibiting the proteolytic activity of trypsin. The improved screening method of the invention comprises the steps of limiting the compounds for screening to trypsin inhibitors and then applying selected trypsin inhibitors to mites (eggs, larvae, adults), either directly or through ingestion, and measuring the survival rate of the mites.

The invention may be better understood by referring to the following examples. The following examples are offered for the purpose of illustrating the invention and should not be interpreted as a limitation of the invention.

EXAMPLES

Example 1

Several compounds having proteinase inhibitory properties were tested for acaricidal activity. 100 ppm aqueous solutions were applied to a mixed population of eggs, larvae, and adults of the following species: *Aphis craccivora*, (Cowpea Aphid); *Nilaparvata lugens*, (Rice Plant Hopper); *Tetranychus urticae*, (Two Spotted Spider Mite); *Spodoptera Littoralls*, (Cotton Leafworm); *Hellothis virescens*, (Tobacco Budworm); *Anthonomus grandis*, (Cotton Boll Weevil); and *Diabrotica balteata*, (Banded Cucumber Beetle). A cotton or bean leaf disk assay was used. Test compounds were applied to leaf disks and allowed to dry prior to the introducing the test organism. The leaves and organisms were left alone for 10 days at 20° C. The experiments were repeated using whole bean plants and lower concentration of the test compounds.

Activity was only observed against *Tetranychus urticae*. Pefabloc (Pentapharm AG) and soybean trypsin inhibitor type 1-S (Sigma, St. Louis, Mo.) were effective against eggs, larvae, and adults. Lima bean trypsin inhibitor (Sigma, St. Louis, Mo.), pentamidine isothionate, and pepstatin A (Sigma, St. Louis, Mo.) were effective against larvae and adults. Aprotinin (Sigma, St. Louis, Mo.) was only effective against adults. The whole bean plant assay demonstrated that soybean trypsin inhibitor was active at 12.5 ppm against *Tetranychus urticae*.

Example 2

The effects of guanidine hydrochloride on *Tetranychus urticae* (two-spotted spider mite) were tested in field experiments on strawberries. The experiments were performed several times. The experimental results are given below in tables 1-5. Each table represents a different point in time. Table 1 represents the earliest observed results; each subsequent table represent a point in time three weeks later than the previous table. The experiments involved applying an equal number of mites to treated strawberry plants. The survival of the mites was measured. A control in which no acaracide was present was used. Similarly, an internal control employing a known acaracide was used. The column labeled "TSM" indicates the average number of surviving mites.

TABLE 1

| | | TSM |
|---|---|---|
| A | 1 | 213 - control |
| | 2 | 177 - guanidine hydrochloride |
| | 3 | 0 - internal control |
| B | 1 | 139 - control |
| | 2 | 100 - guanidine hydrochloride |
| | 3 | 0 - internal control |
| C | 1 | 146 - control |
| | 2 | 14.1 - guanidine hydrochloride |
| | 3 | 0 - internal control |
| D | 1 | 165 - control |
| | 2 | 67 - guanidine hydrochloride |
| | 3 | 0 - internal control |

TABLE 2

| | | TSM |
|---|---|---|
| A | 1 | 343.2 - control |
| | 2 | 228 - guanidine hydrochloride |
| | 3 | 100.8 - guanidine hydrochloride |
| | 4 | 249.2 - internal control |
| B | 1 | 465.6 - control |
| | 2 | 168 - guanidine hydrochloride |
| | 3 | 81 - guanidine hydrochloride |
| | 4 | 187.2 - internal control |

TABLE 2-continued

| | | TSM |
|---|---|---|
| C | 1 | 180 - control |
| | 2 | 240 - guanidine hydrochloride |
| | 3 | 264 - guanidine hydrochloride |
| | 4 | 396 - internal control |
| D | 1 | 211.2 - control |
| | 2 | 108 - guanidine hydrochloride |
| | 3 | 96 - guanidine hydrochloride |
| | 4 | 206.4 - internal control |

TABLE 3

| | | TSM |
|---|---|---|
| A | 1 | 264 - control |
| | 2 | 201.6 - guanidine hydrochloride |
| | 3 | 193.2 - guanidine hydrochloride |
| | 4 | 15 - internal control |
| B | 1 | 278.4 - control |
| | 2 | 88.8 - guanidine hydrochloride |
| | 3 | 53.4 - guanidine hydrochloride |
| | 4 | 22.8 - internal control |
| C | 1 | 144 - control |
| | 2 | 48 - guanidine hydrochloride |
| | 3 | 134.4 - guanidine hydrochloride |
| | 4 | 13.2 - internal control |
| D | 1 | 66 - control |
| | 2 | 90 - guanidine hydrochloride |
| | 3 | 10.8 - guanidine hydrochloride |
| | 4 | 4.8 - internal control |

TABLE 4

| | | TSM |
|---|---|---|
| A | 1 | 156 - control |
| | 2 | 105.6 - guanidine hydrochloride |
| | 3 | 74.4 - internal control |
| B | 1 | 213.6 - control |
| | 2 | 198.8 - guanidine hydrochloride |
| | 3 | 30.6 - internal control |
| C | 1 | 400 - control |
| | 2 | 165 - guanidine hydrochloride |
| | 3 | 76.8 - internal control |
| D | 1 | 184.8 - control |
| | 2 | 136.8 - guanidine hydrochloride |
| | 3 | 54 - internal control |

TABLE 5

| | | TSM |
|---|---|---|
| A | 1 | 80.4 - control |
| | 2 | 27 - guanidine hydrochloride |
| | 3 | 0 - internal control |
| B | 1 | 37.8 - control |
| | 2 | 14.4 - guanidine hydrochloride |
| | 3 | 0 - internal control |
| C | 1 | 25.8 - control |
| | 2 | 8.4 - guanidine hydrochloride |
| | 3 | 0 - internal control |
| D | 1 | 36.6 - control |
| | 2 | 12.6 - guanidine hydrochloride |
| | 3 | 0 - internal control |

INCORPORATION BY REFERENCE

All patents, patents applications, and publications cited are incorporated herein by reference.

EQUIVALENTS

The foregoing written specification is considered to be sufficient to enable one skilled in the art to practice the invention. Indeed, various modifications of the above-described makes for carrying out the invention which are obvious to those skilled in the field of organic chemistry or related fields are intended to be within the scope of the following claims.

What is claimed is:

1. A method of treating a plant infested with mites, said method comprising the step of applying an acaricidally effective amount of guanidine to said plant to reduce mite infestation.

2. The method according to claim 1, wherein the guanidine is guanidine hydrochloride.

3. The method according to claim 1, wherein said mites belong to a Tetranychus species.

4. The method according to claim 3, wherein said mites are *Tetranychus urticae*.

5. The method according to claim 1, wherein said plant is a strawberry.

* * * * *